US009494558B2

(12) United States Patent
Kawata et al.

(10) Patent No.: US 9,494,558 B2
(45) Date of Patent: Nov. 15, 2016

(54) FLAW-DETECTION APPARATUS AND FLAW-DETECTION METHOD

(75) Inventors: Kayoko Kawata, Tokyo (JP); Masaaki Kurokawa, Tokyo (JP); Masayoshi Higashi, Tokyo (JP); Masaya Takatsugu, Tokyo (JP); Yoshihiro Asada, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 725 days.

(21) Appl. No.: 13/387,070

(22) PCT Filed: Oct. 25, 2010

(86) PCT No.: PCT/JP2010/068815
§ 371 (c)(1),
(2), (4) Date: Jan. 25, 2012

(87) PCT Pub. No.: WO2011/077827
PCT Pub. Date: Jun. 30, 2011

(65) Prior Publication Data
US 2012/0123699 A1    May 17, 2012

(30) Foreign Application Priority Data
Dec. 22, 2009   (JP) ................. 2009-291264

(51) Int. Cl.
*G01N 27/90*      (2006.01)
(52) U.S. Cl.
CPC ......... *G01N 27/9033* (2013.01); *G01N 27/902* (2013.01); *G01N 27/904* (2013.01); *G01N 27/9046* (2013.01)
(58) Field of Classification Search
CPC .................................................. G01N 27/902
(Continued)

(56) References Cited

U.S. PATENT DOCUMENTS 4,715,709 A  *  12/1987  Sekine et al. ............. 356/237.2
4,763,274 A       8/1988  Junker et al.
(Continued)

FOREIGN PATENT DOCUMENTS

JP       5-281199 A     10/1993
JP       6-82425 A      3/1994
(Continued)

OTHER PUBLICATIONS

Decision to Grant a Patent dated May 13, 2014, issued in corresponding Japanese Patent Application No. 2009-291264, with concise English language explanation of relevance, the Decision to Grant a Patent has been received.
(Continued)

*Primary Examiner* — Regis Betsch
(74) *Attorney, Agent, or Firm* — Westerman, Hattori, Daniels & Adrian, LLP

(57) ABSTRACT

Noise included in detection signals is distinguished with a simple configuration. Provided is a flaw-detection apparatus (1) including a flaw-detection sensor group (11) in which two flaw-detection sensors (11a and 11b) are arranged substantially in one row in a scanning direction with a distance therebetween and a processing device (15) that detects a defect in an inspection object on the basis of detection signals detected by the individual flaw-detection sensors (11a and 11b), wherein, with regard to the detection signals detected by the flaw-detection sensors (11a and 11b), when signal values detected at substantially a same positional coordinate in the scanning direction are not similar to each other, and, additionally, when signal values measured at a same time are similar to each other, the processing device (15) determines that the detection signals are not defect signals.

7 Claims, 14 Drawing Sheets

(58) Field of Classification Search
USPC .......................................................... 702/35
See application file for complete search history.

(56) References Cited

U.S. PATENT DOCUMENTS

| | | | |
|---|---|---|---|
| 4,876,506 A | | 10/1989 | Brown et al. |
| 5,371,462 A | | 12/1994 | Hedengren et al. |
| 5,623,203 A | * | 4/1997 | Hosohara et al. ............ 324/220 |
| 6,501,267 B1 | | 12/2002 | Kurokawa et al. |
| 7,402,999 B2 | * | 7/2008 | Plotnikov et al. ............ 324/220 |
| 2002/0003421 A1 | * | 1/2002 | Kawata et al. ................ 324/233 |
| 2003/0164700 A1 | * | 9/2003 | Goldfine ................ G01N 27/82 324/235 |
| 2006/0288756 A1 | * | 12/2006 | De Meurechy ................ 73/1.01 |
| 2008/0159619 A1 | | 7/2008 | Suh et al. |
| 2010/0127699 A1 | | 5/2010 | Wang et al. |
| 2011/0167914 A1 | * | 7/2011 | Sutherland ..................... 73/643 |

FOREIGN PATENT DOCUMENTS

| | | | |
|---|---|---|---|
| JP | 6-194321 A | | 7/1994 |
| JP | 7-190991 A | | 7/1995 |
| JP | 9-166582 A | | 6/1997 |
| JP | 11-51906 A | | 2/1999 |
| JP | 11-258211 A | | 9/1999 |
| JP | 2000-2689 A | | 1/2000 |
| JP | 2000-227421 A | | 8/2000 |
| JP | 2000-227422 A | | 8/2000 |
| JP | 2000-275219 A | | 10/2000 |
| JP | 2000-356624 A | | 12/2000 |
| JP | 2003-344360 A | | 12/2003 |
| JP | 2006-138784 A | | 6/2006 |
| JP | 2007-263930 A | | 10/2007 |
| JP | 2008-46069 A | | 2/2008 |
| JP | 2008-309573 A | | 12/2008 |
| JP | 2009-19909 A | | 1/2009 |
| WO | 00/08458 A1 | | 2/2000 |
| WO | PCT/IB2009/006499 | * | 6/2009 ............. G01N 29/04 |

OTHER PUBLICATIONS

International Search Report of PCT/JP2010/068815, date of mailing; Jan. 18, 2011.

* cited by examiner

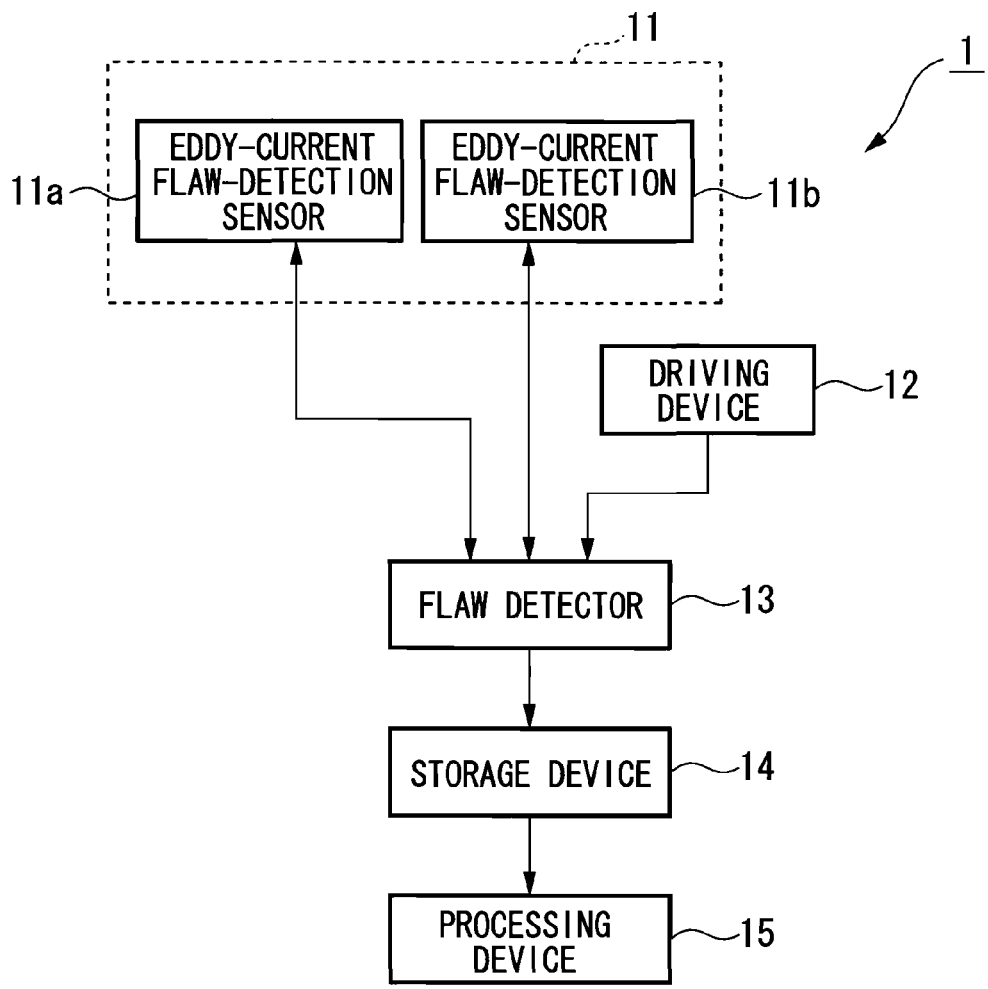
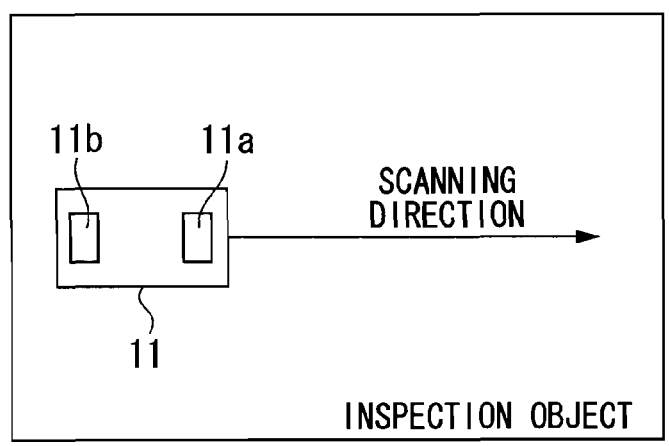

FIG. 7
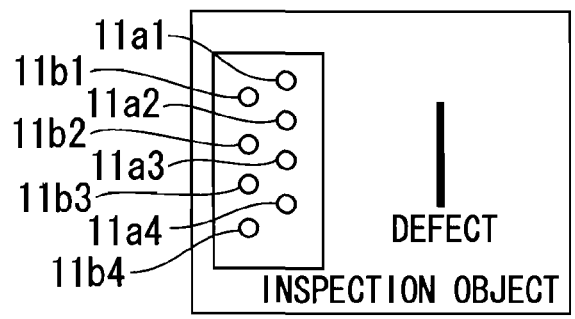
(a)
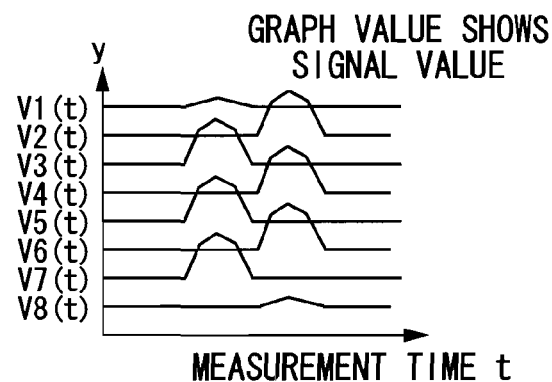
(b)
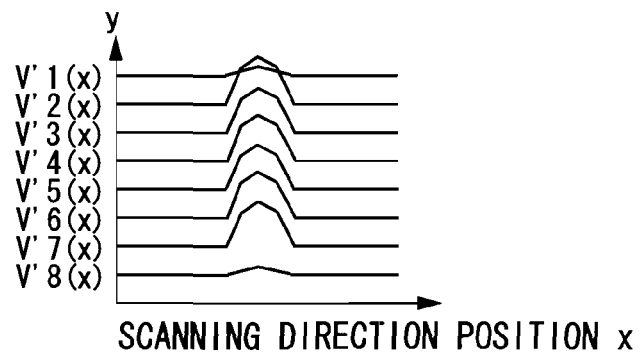
(c)
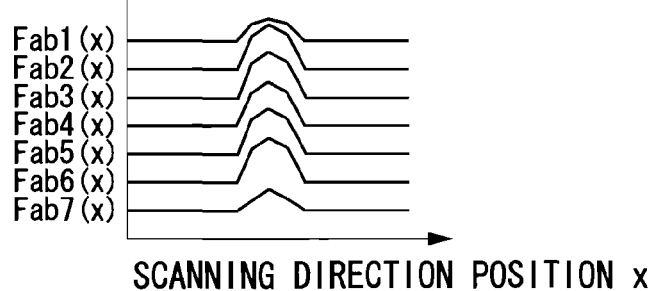
(d)

FIG. 14
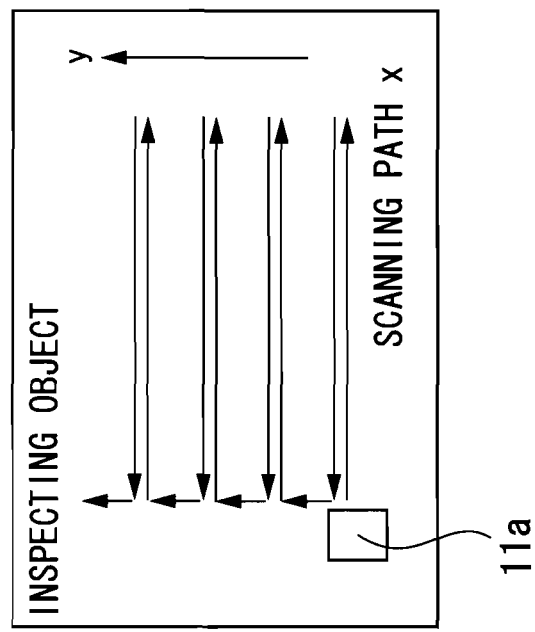
(a)
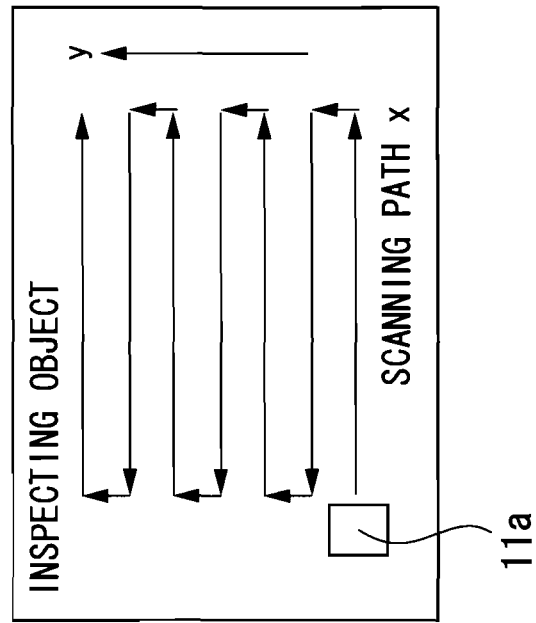
(b)

FLAW-DETECTION APPARATUS AND FLAW-DETECTION METHOD

TECHNICAL FIELD

The present invention relates to a flaw-detection apparatus and flaw-detection method for non-destructive inspection, such as eddy-current flaw detection, ultrasonic flaw detection, etc., for a defect, such as a crack or the like, that occurs in an inspection object.

BACKGROUND ART

Known methods for non-destructively inspecting an inspection object for a defect, such as a crack or the like, that occurs therein include the eddy-current flaw detection method (ECT: Eddy Current Testing) and the ultrasonic flaw detection method (UT: Ultrasonic Testing).

The eddy-current flaw detection method is a technique in which an eddy current is generated in an inspection object by generating flux changes with an exciting coil supplied with an excitation current; additionally, detection signals that represent the flux generated by this eddy current are obtained as output signals from a detection coil; and the position, shape, depth, etc. of the defect (damage) in the inspection object are determined on the basis of these detection signals.

Although the eddy-current flaw detection method performs flaw detection by detecting changes in the intensity and current pattern of the eddy current caused by the defect in the inspection object, changes in such intensity and current pattern of the eddy current are caused not only by the defect in the inspection object but also by changes in coil impedance due to fluctuations in the electrical resistivity and magnetic permeability of the inspection object, the coil orientation (distance and angle relative to the inspection object), and so on. Therefore, such changes in the coil impedance appear in the detection signals as noise, and deterioration of flaw-detection precision due to this noise has been a problem.

In the related art, for example, methods like the following have been proposed as methods for discriminating noise included in detection signals.

For example, Patent Literature 1 discloses a technique wherein, in a defect distinguishing method in which a damage signal and a noise signal are distinguished by using detection signals obtained with an eddy-current flaw-detection multiprobe in which detection coils and exciting coils are disposed side by side, X-scan signals from the exciting coils and the detection coils that are disposed in one direction of the multiprobe and Y-scan signals from the exciting coils and the detection coils that are disposed in another direction are calculated as phase angles; the calculated phase angles are plotted on a graph by setting the X-scan phase angle on the horizontal axis and the Y-scan phase angle on the vertical axis; and the noise signals included in the detection signals are distinguished based on differences in characteristics of individual detection signal extents on the graph.

Patent Literature 2 discloses noise discrimination in which a distance sensor is added to measure a distance between the sensor and a surface of the inspection object, and noise included in the detection signals is distinguished by determining whether a change occurs in the distance based on measurement results from the distance sensor.

Patent Literature 3 discloses a technique in which a normal probe 11 and a magnetic saturation probe 13 which reduces noise due to changes in magnetic permeability with a magnet provided therein are provided; signal waveforms obtained by scanning the same location with the normal probe and the magnetic saturation probe are comparatively analyzed with a processing apparatus; and a distinction is made as to whether the signal waveforms are caused by damage in the inspection object, which is a measurement target, or are caused by noise.

CITATION LIST

Patent Literature

{PTL 1} Japanese Unexamined Patent Application, Publication No. 2009-19909.
{PTL 2} Japanese Unexamined Patent Application, Publication No. 2006-138784.
{PTL 3} Japanese Unexamined Patent Application, Publication No. 2008-309573.

SUMMARY OF INVENTION

Technical Problem

However, with the method disclosed in Patent Literature 1 described above, there is a problem in that the noise signals cannot be distinguished when noise components that appear in the detection signals have emergence patterns that are highly similar to those of the detection signals. For example, because noise caused by changes in the distance between the sensor and the inspection object or an inclination thereof has waveform characteristics that are highly similar to those of a shallow opening defect, in such a case, it is not possible to distinguish whether it is due to the opening defect or due to noise.

With the method disclosed in Patent Literature 2 described above, there is a problem in that the apparatus becomes complex because the distance sensor must be added. Furthermore, even if the distance can be measured accurately with the distance sensor, it is difficult to accurately estimate noise waveforms of ECT signals on the basis of the measured distance; therefore, it is difficult to distinguish whether or not the measured ECT signals include defects.

With the method disclosed in Patent Literature 3 described above, noise cannot be identified in the detection signals in the case in which the noise and defects are occurring at the same time.

The present invention has been conceived in light of the above-described circumstances, and an object thereof is to provide a flaw-detection apparatus and a flaw-detection method that are capable of distinguishing noise included in detection signals with a simple configuration.

Solution to Problem

In order to solve the above-described problems, the present invention employs the following solutions.

A first aspect of the present invention provides a flaw-detection apparatus including a flaw-detection sensor group in which a plurality of flaw-detection sensors are arranged substantially in one row in a scanning direction with a distance therebetween; and a processing device that detects a defect in an inspection object on the basis of detection signals detected by the individual flaw-detection sensors, wherein, with regard to the detection signals detected by the individual flaw-detection sensors, when signal values detected at substantially a same positional coordinate in the scanning direction are not similar to each other, and, additionally, when signal values measured at a same time are similar to each other, the processing device determines that the detection signals are not defect signals.

With such a configuration, the plurality of the flaw-detection sensors are disposed in substantially one row in the scanning direction with a distance therebetween; and, with regard to the detection signals detected by the flaw-detection sensors, when the signal values detected at substantially the same positional coordinate in the scanning direction are not similar to each other, and, additionally, when the signal values measured at the same time are similar to each other, the detection signals are determined not to be defect signals; therefore, noise components generated due to causes other than a defect, such as a deformation, etc., and signal components due to the defect can be distinguished from each other with a simple configuration.

The above description "disposed in substantially one row" represents a concept which includes a case in which the adjacent flaw-detection sensors are disposed slightly shifted within a range where the distance therebetween is smaller than the extent (that is, a length perpendicular to the scanning direction) of targeted defect signals.

With the above-described flaw-detection apparatus, with regard to the detection signals detected by the individual flaw-detection sensors, the processing device may compare signal values detected at substantially the same positional coordinate in the scanning direction with each other, may create a filtering signal in which signal values for positions where the signal values have substantially a same value as each other are amplified relative to signal values for positions where the signal values do not have substantially the same value as each other, and may detect the defect in the inspection object on the basis of the filtering signal.

With such a configuration, with regard to the detection signals detected by the individual flaw-detection sensors, the processing device compares the signal values detected at substantially the same coordinate in the scanning direction with each other and creates the filtering signals in which the signal values for positions where the signal values have substantially the same value as each other are amplified relative to the signal values for positions where the signal values do not have substantially the same value as each other; therefore, noise components generated due to causes other than a defect, such as a deformation, etc., can be removed, making it possible to extract only the signal components due to the defect. Accordingly, the detection precision for a defect occurring in the inspection object can be improved with a simple configuration.

With the flaw-detection apparatus described above may have a flaw-detection sensor unit formed of a plurality of the flaw-detection sensor groups disposed along a direction perpendicular to the scanning direction, wherein, with regard to individual detection signals detected by the flaw-detection sensors that constitute the flaw-detection sensor unit, when signal values detected at substantially the same positional coordinate in the scanning direction are not similar to each other, and, additionally, when signal values measured at a same time are similar to each other, the processing device may determine that the detection signals are not defect signals.

Furthermore, with the flaw-detection apparatus described above, with regard to the detection signals detected by the individual flaw-detection sensors that constitute the flaw-detection sensor unit, the processing device may compare signals detected at substantially the same positional coordinate in the scanning direction with each other, may create a filtering signal in which signal values for positions where the signal values have substantially a same value as each other are amplified relative to signal values for positions where the signal values do not have substantially the same value as each other, and may detect the defect in the inspection object on the basis of the filtering signal.

In performing flaw-detection by employing the flaw-detection sensor unit that is constituted of the plurality of flaw-detection sensor groups arranged along the direction perpendicular to the scanning direction, the placement thereof is one of the usual placements for efficiently performing flaw-detection, and a defect and noise can be distinguished from each other without adding a special sensor.

With the flaw-detection apparatus described above, when it is assumed that the scanning direction is an x-axis direction and that the direction perpendicular to the scanning direction is a y-axis direction, the flaw-detection sensor unit may have two rows of the flaw-detection sensors arranged in parallel with respect to y-axis coordinates, and the flaw-detection sensors may be disposed so as to individually take different y-coordinate values; and the processing device may create a plurality of the filtering signals by comparing the detection signals from the flaw-detection sensors whose y-coordinate values are adjacent to each other, and may detect the defect in the inspection object from these filtering signals.

With such a configuration, noise components and components due to a defect can be distinguished from each other with a high precision.

A second aspect of the present invention provides a flaw-detection apparatus including a flaw-detection sensor unit formed by arranging flaw-detection sensor groups formed of a plurality of flaw-detection sensors disposed in substantially one row in a scanning direction with a distance therebetween, along a direction perpendicular to the scanning direction; and a processing device that detects a defect in an inspection object on the basis of detection signals detected by the individual flaw-detection sensors that constitute the flaw-detection sensor unit, wherein the processing device divides the flaw-detection sensors into groups according to rows arranged along a direction perpendicular to the scanning direction, removes common trends appearing in the closely-located detection signals detected by the flaw-detection sensors that belong to the same groups, and detects the defect in the inspection object on the basis of signals after the removal.

For example, in the case in which a deformation occurs in the inspection object, noise due to the deformation simultaneously occurs in the closely-located flaw-detection sensors that constitute the flaw-detection sensor unit. Consequently, when the detection signals detected by the individual flaw-detection sensors are divided into groups on the basis of the placement positions of the flaw-detection sensors in the scanning direction, the same characteristics (for example, peaks) appear at the same time in the detection signals regardless of the groups. Therefore, by performing processing that removes the common characteristics appearing in the closely-located signals which belong to the same groups, it is possible to remove noise components due to orientation changes of the flaw-detection sensors caused by a deformation, etc. On the other hand, in the case in which a defect whose extent is small in the direction perpendicular to the scanning direction of the flaw-detection sensor unit is detected, signal changes due to this defect appear only in some of the flaw-detection sensors that constitute the flaw-detection sensor unit. Accordingly, the same characteristics do not appear in all of the closely-located signals that belong to the same groups.

Therefore, with such a flaw-detection apparatus, a defect whose extent is small in the direction perpendicular to the scanning direction of the flaw-detection sensor unit can effectively be detected with a simple configuration.

With the above-described flaw-detection apparatus, the processing device may determine signals at measurement positions of flaw-detection signals by interpolation for the individual groups, may create combined signals that correspond to the individual flaw-detection sensors by taking averages between the groups for the interpolated signals, and may detect the defect in the inspection object on the basis of the combined signals.

When the detection signals detected by the individual flaw-detection sensors are processed by dividing them into groups, residual components of noise in the obtained signals, etc. sometimes form discontinuous, unnatural signals. Therefore, processing is performed in which the detection signals in the individual groups are interpolated, averages are taken between the groups, and then, the common characteristics in the closely-located signals are reduced, thereby making the processed signals smooth, and thus, the flaw-detection precision can be further improved.

A third aspect of the present invention provides a flaw-detection apparatus including a flaw-detection sensor that reciprocatingly scans over an inspection object; and a processing device that detects a defect in the inspection object on the basis of detection signals detected by the flaw-detection sensor, wherein, with regard to the detection signals detected by the flaw-detection sensor, when signal values detected at substantially a same positional coordinate in the scanning direction are not similar to each other, and, additionally, when signal values measured at a same time are similar to each other, the processing device determines that the detection signals are not defect signals.

Furthermore, with the flaw-detection apparatus described above, with regard to the detection signals detected by the flaw-detection sensor, the processing device may compare signals detected at substantially the same positional coordinate in the scanning direction with each other, may create a filtering signal in which signal values for positions where the signal values have substantially a same value as each other are amplified relative to signal values for positions where the signal values do not have substantially the same value as each other, and may detect the defect in the inspection object on the basis of the filtering signal.

With such a configuration, because it suffices to have one flaw-detection sensor, high-precision flaw detection can be performed with an extremely simple configuration.

A fourth aspect of the present invention provides a flaw-detection method in which a plurality of flaw-detection sensors are arranged in substantially one row in a scanning direction with a distance therebetween, and in which a defect in an inspection object is detected on the basis of detection signals detected by the individual flaw-detection sensors, wherein, with regard to the detection signals detected by the individual flaw-detection sensors, when signal values detected at substantially a same positional coordinate in the scanning direction are not similar to each other, and, additionally, when signal values measured at a same time are similar to each other, the detection signals are determined not to be defect signals.

Furthermore, with the flaw-detection method described above, with regard to the detection signals detected by the individual flaw-detection sensors, signals detected at substantially the same positional coordinate in the scanning direction may be compared with each other, a filtering signal may be created in which signal values for positions where the signal values have substantially a same value as each other are amplified relative to signal values for positions where the signal values do not have substantially the same value as each other, and the defect in the inspection object may be detected on the basis of the filtering signal.

A fifth aspect of the present invention provides a flaw-detection method in which a flaw-detection sensor unit is formed by arranging flaw-detection sensor groups formed of a plurality of flaw-detection sensors disposed in substantially one row in a scanning direction with a distance therebetween, along a direction perpendicular to the scanning direction, and in which a defect in an inspection object is detected on the basis of detection signals detected by the individual flaw-detection sensors that constitute the flaw-detection sensor unit, wherein the plurality of the flaw-detection sensors are divided into groups according to rows arranged along the direction perpendicular to the scanning direction, common trends appearing in the closely-located detection signals detected by the flaw-detection sensors that belong to same groups are removed, and the defect in the inspection object is detected on the basis of signals after the removal.

A sixth aspect of the present invention provides a flaw-detection method in which a flaw-detection sensor is reciprocatingly scanned at a surface of an inspection object, and in which a defect in the inspection object is detected on the basis of detection signals detected by the flaw-detection sensor, wherein, with regard to the detection signals detected by the flaw-detection sensor, when signal values detected at substantially a same positional coordinate in the scanning direction are not similar to each other, and, additionally, when signal values measured at a same time are similar to each other, the detection signals are determined not to be defect signals.

Furthermore, with the flaw-detection method described above, signal values detected at substantially the same positional coordinate in the scanning direction may be compared with each other, a filtering signal may be created, in which signal values for positions where the signal values have substantially a same value as each other are amplified relative to signal values for positions where the signal values do not have substantially the same value as each other, and the defect in the inspection object may be detected on the basis of the filtering signal.

Advantageous Effects of Invention

With the present invention, an advantage is afforded in that noise included in detection signals can be distinguished with a simple configuration.

BRIEF DESCRIPTION OF DRAWINGS

FIG. 1 is a diagram showing, in outline, the configuration of a flaw-detection apparatus according to a first embodiment of the present invention.

FIG. 2 is a diagram for explaining the placement of flaw-detection sensors in a flaw-detection sensor group.

FIG. 7 is a diagram for explaining processing executed by a processing device according to the second embodiment of the present invention.

FIG. 14 is a diagram showing a configuration example of the flaw-detection apparatus according to the present invention.

DESCRIPTION OF EMBODIMENTS

Figure 3:
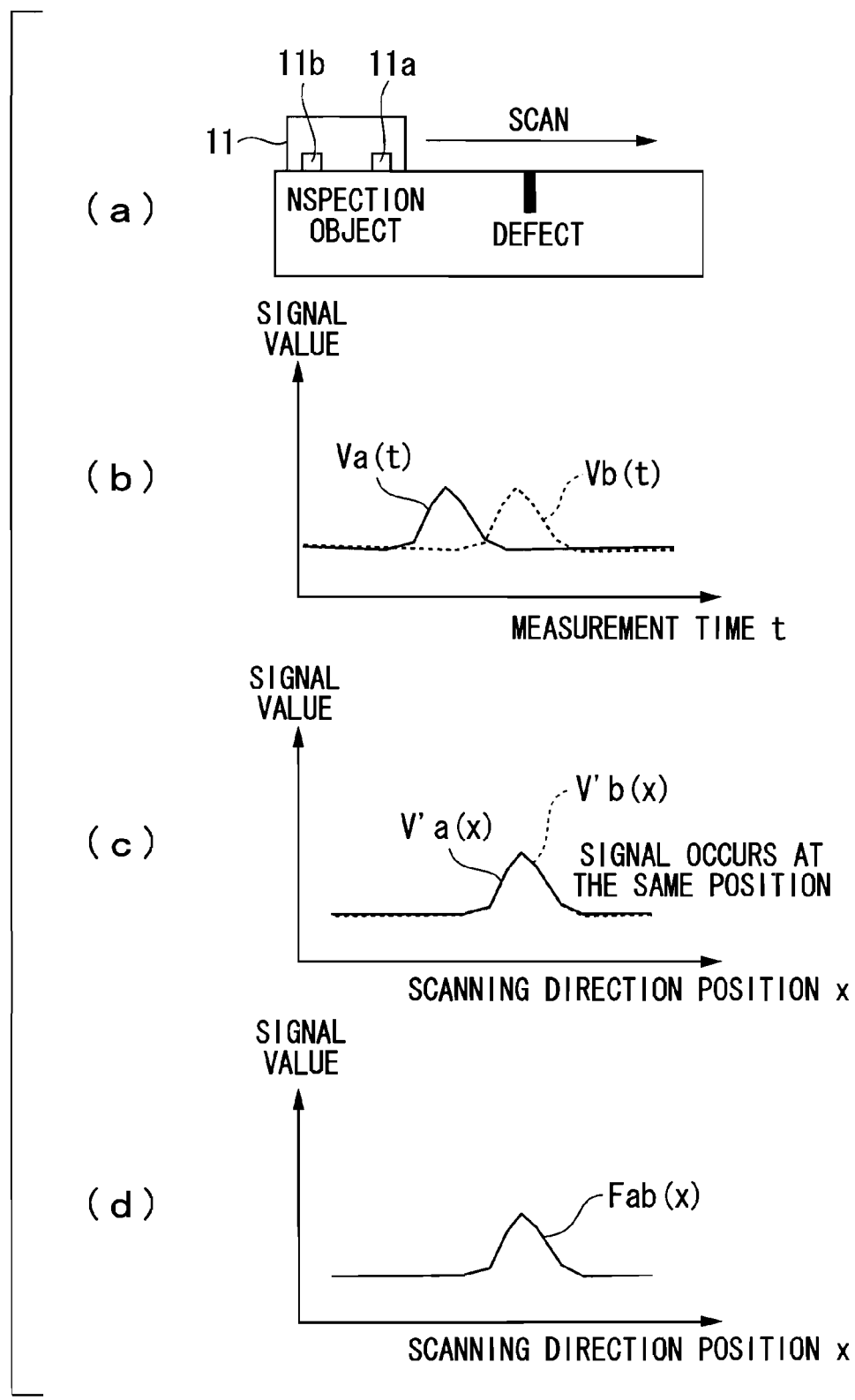
FIG. 3 is a diagram for explaining processing executed by a processing device according to the first embodiment of the present invention.

Flaw-detection apparatuses and flaw-detection methods according to embodiments of the present invention will be described below with reference to the drawings. Although the flaw-detection apparatuses and the flaw-detection methods according to the present invention are widely applicable to flaw-detection methods such as the eddy-current flaw detection method, ultrasonic flaw detection, etc. for non-destructively inspecting an inspection object for a defect such as a crack or the like occurring therein, for the sake of convenience, cases in which it is applied to the eddy-current flaw detection method will be described below as examples.
{First Embodiment}

FIG. 1 is a diagram showing, in outline, the configuration of a flaw-detection apparatus 1 according to a first embodiment of the present invention. In FIG. 1, the flaw-detection apparatus 1 is provided with a flaw-detection sensor group 11 having two eddy-current flaw detection sensors (hereinafter, referred to as "flaw-detection sensors") 11a and 11b, a driving device 12, a flaw detector 13, a storage device 14, and a processing device 15.

As shown in FIG. 2, the flaw-detection sensors 11a and 11b are disposed in a row with a distance therebetween in a scanning direction; the flaw-detection sensor 11a is disposed forward in the scanning direction, and the flaw-detection sensor 11b is disposed rearward in the scanning direction. The flaw-detection sensors 11a and 11b are generally employed in the eddy-current flaw detection method for the maintenance inspection of piping, etc., and, for example, sensors of a differential type are employed.

The driving device 12 scans the flaw-detection sensors 11a and 11b, is provided with a position detector such as an encoder or the like, and outputs position signals to the flaw detector 13. The flaw detector 13 excites coils in the flaw-detection sensors 11a and 11b, obtains output signals from the coils as detection signals, also obtains the position signals from the driving device 12, and outputs them to the storage device 19 after A/D conversion of these signals.

The storage device 14 sequentially records the position signals and the detection signals from the flaw detector 13. With regard to the detection signals detected by the individual flaw-detection sensors 11a and 11b, the processing device 15 compares signal values detected at the same scanning positions with each other, generates filtering signals in which the signal values for positions where the two signal values have substantially the same values are amplified relative to the signal values for positions where the two values do not have substantially the same values, and a defect in an inspection object is detected on the basis of the filtering signals.

Defect detection by the processing device 15 will be specifically described below with reference to the drawings.

As shown in FIG. 3(a), for example, when a defect C occurs in the inspection object, the detection signals detected by the flaw-detection sensors 11a and 11b take waveforms like those shown in FIG. 3(b). In FIG. 3(b), the horizontal axis is the measurement time, the vertical axis is the signal value, the solid line Va(t) indicates the detection signal from the flaw-detection sensor 11a, and the broken line Vb(t) indicates the detection signal from the flaw-detection sensor 11b. As shown FIG. 2, because the flaw-detection sensors 11a and 11b are arranged side-by-side with a distance therebetween in the scanning direction, a time lag occurs in detection of the defect C. Although the ECT signals take complex numbers, the figure conceptually shows the real part or the imaginary part thereof. This also applies in the following descriptions.

Next, the individual detection signals shown in FIG. 3(b) are corrected so that respective positions in the scanning direction (scanning positions) are matched, and thus, sensor-position corrected signals are obtained. In other words, the time-series detection signals are converted to signals for the individual scanning positions. By doing so, waveforms like those shown in FIG. 3(c) are obtained. In FIG. 3(c), the horizontal axis is the scanning-direction position, the vertical axis is the signal value, and the sensor-position corrected signals that correspond to the two flaw-detection sensors are matched. In this way, when the defect C occurs, similar signal values (waveforms) are obtained at a scanning position (X-coordinate value) where the defect C occurs. Subsequently, the processing device 15 enhances (amplifies), relative to signal values for positions where two signals are not substantially the same value, the signal values for positions where two signal values are substantially the same value when the individual signal values of the sensor-position corrected signals are compared for the individual scanning positions, and thereby, a filtering signal such as the one shown in FIG. 3(d) is generated. This filtering is similarly applied to the real part and the imaginary part in the sensor-position corrected signals. This also applies in the following descriptions.

For example, the processing device 15 performs a calculation as shown in the following Expression (1) and generates the filtering signal by taking a cross-correlation between the two signals.

$$Fab(x)=sign(V'a(x))*sqrt(|V'a(x)*V'b(x)|) \quad (1)$$

In the Expression (1) above, Fab(x) is the filtering signal, V'a(x) is the signal value of the sensor-position corrected signal from the flaw-detection sensor 11a, and V'b(x) is the signal value of the sensor-position corrected signal from the flaw-detection sensor 11b. In addition, sign(X) is the sign of X, |X| is the absolute value of X, and sqrt(X) is the square root of X.

In the case in which the defect C is assumed, because the signal values from the flaw-detection sensor 11a and 11b take substantially the same value at the position where the defect C occurs, the filtering signal obtained at the scanning position for the defect C is substantially equivalent to the two signal values, as shown in FIG. 3(d).

Figure 4:
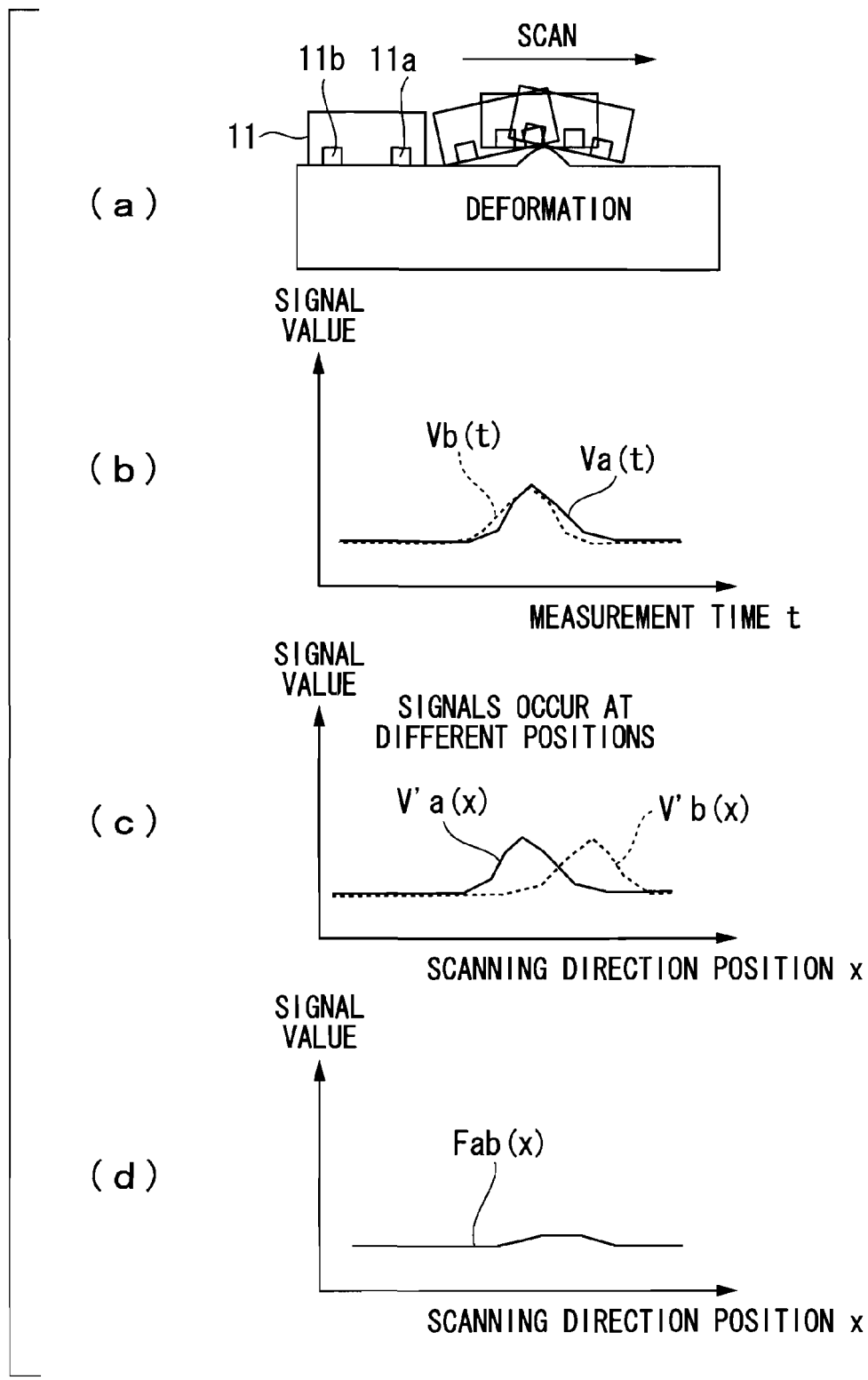
FIG. 4 is a diagram for explaining the processing executed by the processing device according to the first embodiment of the present invention.

In contrast, for example, as shown in FIG. 4(a), when a deformation occurs in the inspection object, signal changes due to the deformation occur at the same time in the flaw-detection sensors 11a and 11b, as shown in FIG. 4(b). This is because the flaw-detection sensors 11a and 11b are integrated and because if one of them changes orientation due to the deformation, the other necessarily experiences its effect.

Therefore, in the case in which a deformation occurs in the inspection object, signal value peaks appear in the sensor-position corrected signals from the individual flaw-detection sensors 11a and 11b at different scanning positions, as shown in FIG. 4(c). Therefore, a filtering signal obtained from such sensor-position corrected signals takes a waveform like the one shown in FIG. 4(d), which is a signal from which noise due to the deformation has been removed.

Figure 5:
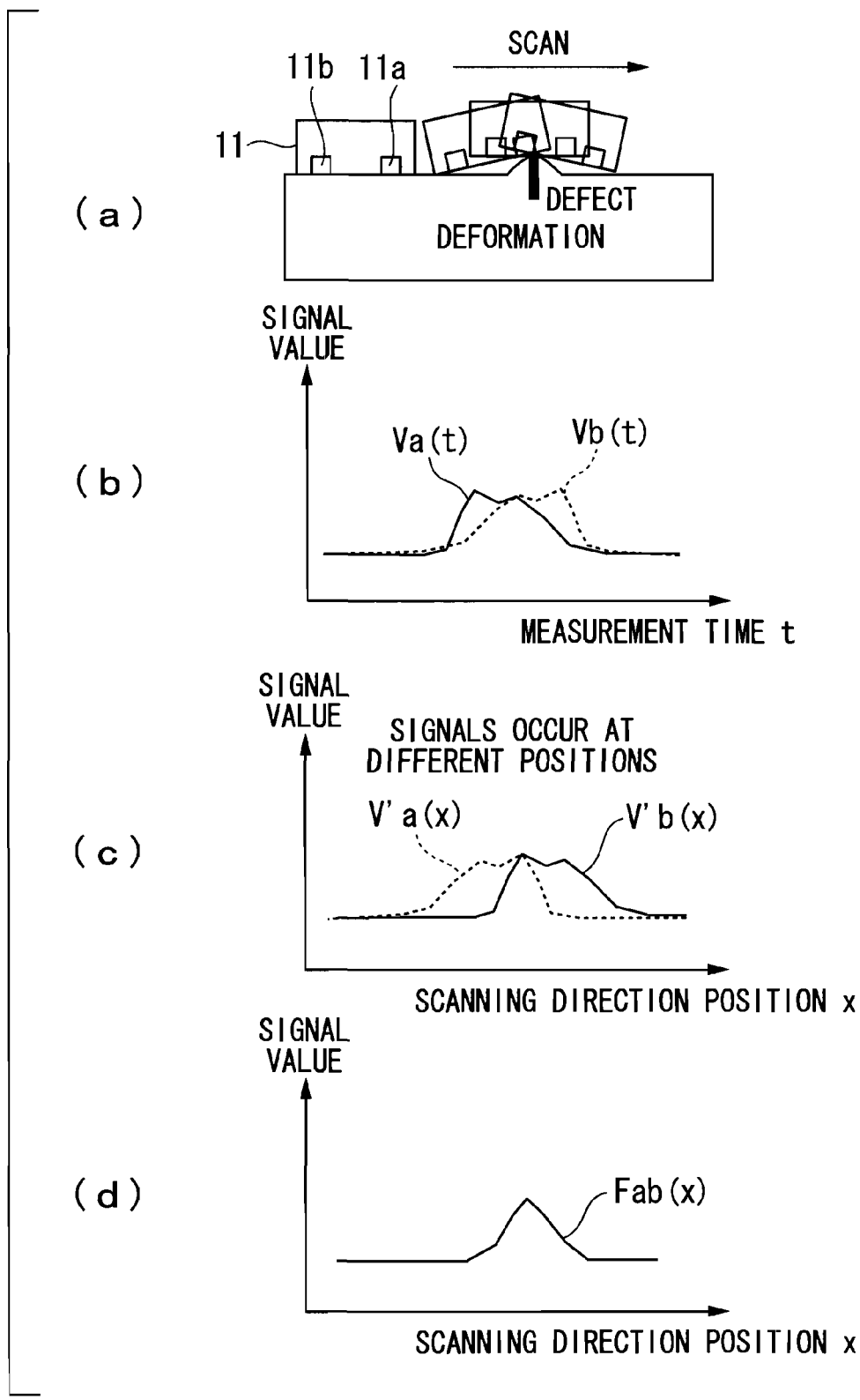
FIG. 5 is a diagram for explaining the processing executed by the processing device according to the first embodiment of the present invention.

In addition, for example, as shown in FIG. 5(a), in the case in which a deformation and a defect occur at the same position in the inspection object, the detection signals such as those shown in FIG. 5(b) are obtained, and sensor-position corrected signals such as those shown in FIG. 5(c) are obtained from these detection signals. As a result, a filtering signal such as the one shown in FIG. 5(d) is obtained. In this way, even in the case in which the deformation and the defect have occurred at the same position, noise components due to the deformation can be removed, making it possible to extract only the signal values due to the defect.

As described above, the flaw-detection apparatus and the flaw-detection method according to this embodiment have been proposed focusing on the fact that the same signal value is obtained at the same scanning position in the case of the signal values due to a defect, whereas noise caused by the orientation changes in the flaw-detection sensor group due to a deformation, etc. occurs at the same time, and thus, the same signal value is not obtained at the same scanning position. Specifically, the two flaw-detection sensors 11a and 11b are disposed in one row in the scanning direction with a distance therebetween; with regard to the detection signals detected by the flaw-detection sensors 11a and 11b, the signal values detected at the same scanning position (in other words, signal values at the same x-coordinate value) are compared with each other; the filtering signal is generated, in which the signal values for the positions where the two signal values have substantially the same value are amplified relative to the signal values for the positions where the two values do not have substantially the same value; and the defect is evaluated on the basis of this filtering signal. Accordingly, the noise components due to causes other than a defect, such as a deformation, etc., can be removed from the filtering signal, making it possible to extract only the signal components due to the defect. As a result, the detection precision for a defect occurring in the inspection object can be improved.

Although the cross-correlation is employed when obtaining the filtering signal in this embodiment, the method for obtaining the filtering signal is not limited thereto. For example, as shown in Expression (2) below, an average value may be taken between the two signal values, or, as shown in Expression (3) below, a signal having the same sign as one of the signals that takes the smallest value between the absolute values of the two signal values may be used.

$$Fab(x)=(V'a(x)+V'b(x))/2 \qquad (2)$$

$$Fab(x)=sign(V'a(x))*min(|V'a(x)|,|V'b(x)|) \qquad (3)$$

In this embodiment, although a case in which the flaw-detection sensor group 11 is formed of the two flaw-detection sensors 11a and 11b has been described in this embodiment, there is no particular limitation with regard to the number of flaw-detection sensors that constitute the flaw-detection sensor group 11.

Although a case in which the two flaw-detection sensors 11a and 11b are disposed in one row has been described, the two flaw-detection sensors 11 and 11b may be disposed slightly shifted in a direction perpendicular to the scanning direction. In this case, a shift width is set to be smaller than the extent (that is, the length perpendicular to the scanning direction) of targeted defect signals.

{Second Embodiment}

Next, a flaw-detection apparatus and a flaw-detection method according to a second embodiment of the present invention will be described.

Figure 6:
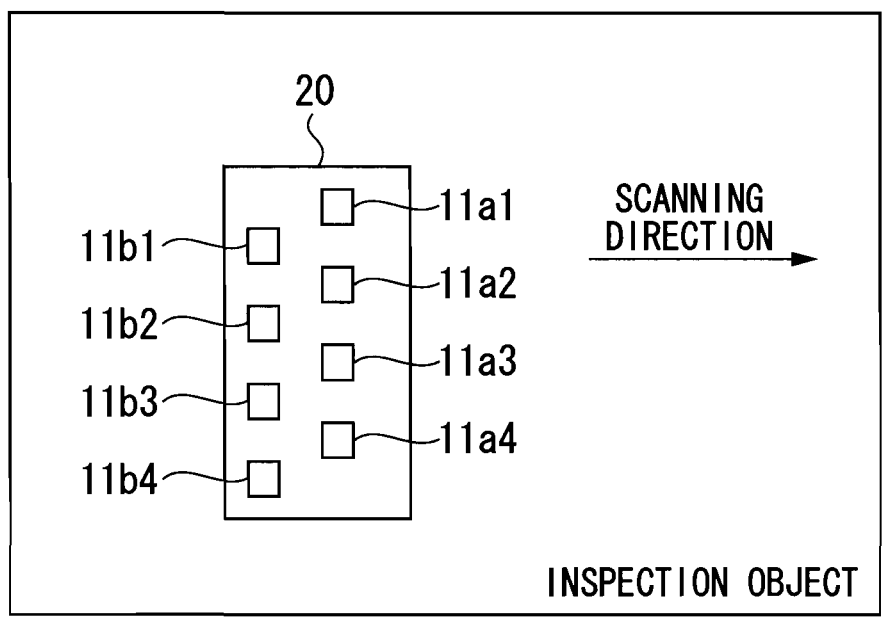
FIG. 6 is a diagram for explaining a flaw-detection sensor unit of a flaw-detection apparatus according to a second embodiment of the present invention.

Although a case in which one flaw-detection sensor group formed of the plurality of the flaw-detection sensors is provided has been described in the first embodiment, the flaw-detection apparatus according to this embodiment is provided with, for example, as shown in FIG. 6, a flaw-detection sensor unit 20 in which a plurality of the flaw-detection sensor groups 11 are disposed side-by-side in the direction perpendicular to the scanning direction. In the following, the flaw-detection apparatus and the flaw-detection method according to this embodiment will be described mainly with regard to differences from the first embodiment described above.

For example, as shown in FIG. 6, when the scanning direction is defined as the x-axis direction and the direction perpendicular to the scanning direction is defined as the y-axis direction, between the individual flaw-detection sensor groups constituting the flaw-detection sensory unit 20, the individual flaw-detection sensors 11a1, 11a2, 11a3, and 11a4 disposed forward in the scanning direction are disposed so as to take y-coordinate values that are different from each other at the same x-coordinate value, and, in addition, the flaw-detection sensors 11b1, 11b2, 11b3, and 11b4 disposed rearward in the scanning direction are disposed so as to take y-coordinate values that are different from each other at the same x-coordinate value.

The processing device creates the filtering signals on the basis of the detection signals detected by the individual flaw-detection sensors 11a1 to 11b4 that constitute the flaw-detection sensor unit 20 and detects the defect in the inspection object. Specifically, as shown in FIG. 7(a), in the case in which a defect whose extent is longer in the direction (y-axis direction) perpendicular to the scanning direction occurs, the detection signals obtained by the individual flaw-detection sensors 11a1 to 11b4 take waveforms like those shown in FIG. 7(b). In FIG. 7(b), the horizontal axis is the measurement time, and the detection signals detected by the individual flaw-detection sensors are vertically arranged along the vertical axis so as to correspond with the placement positions of the individual flaw-detection sensors on the inspection object.

In FIG. 7(b), V1(t) is the detection signal obtained by the flaw-detection sensor 11a1, V2(t) is the detection signal obtained by the flaw-detection sensor 11b1, V3(t) is the detection signal obtained by the flaw-detection sensor 11a2, V4(t) is the detection signal obtained by the flaw-detection sensor 11b2, V5(t) is the detection signal obtained by the flaw-detection sensor 11a3, V6(t) is the detection signal obtained by the flaw-detection sensor 11b3, V7(t) is the detection signal obtained by the flaw-detection sensor 11a4, and V8(t) is the detection signal obtained by the flaw-detection sensor 11b4.

Next, the processing device obtains sensor-position corrected signals by correcting the detection signals V1(t) to V8(t). The sensor-position corrected signals that correspond to FIG. 7(b) are shown in FIG. 7(c). Then, the processing device creates filtering signals on the basis of these sensor-position corrected signals.

For example, in the case in which only the y-coordinate values are taken into consideration for the placement positions of the individual flaw-detection sensors, the processing device may create the filtering signals by comparing the sensor-position corrected signals for the flaw-detection sensors that are adjacent to each other. For example, as shown in FIG. 6, when only the positions on the y-axis are taken into consideration, the flaw-detection sensors are arranged from one end in the order of the flaw-detection sensors 11a1, 11b1, 11a2, 11b2, 11a3, 11b3, 11a4, and 11b4. Therefore, pairs of adjacent flaw-detection sensors are pairs 11a1 and 11b1, 11b1 and 11a2, 11a2 and 11b2 . . . , and 11a4 and 11b4. The processing device creates individual filtering signals by comparing the sensor-position corrected signals for these adjacent flaw-detection sensors with each other. As a result, for example, the filtering signals Fab1 to Fab7 such as those shown in FIG. 7(d) are obtained. The processing device detects the defect that occurs in the inspection object on the basis of the filtering signals Fab1 to Fab7 shown in FIG. 7(d).

Figure 8:
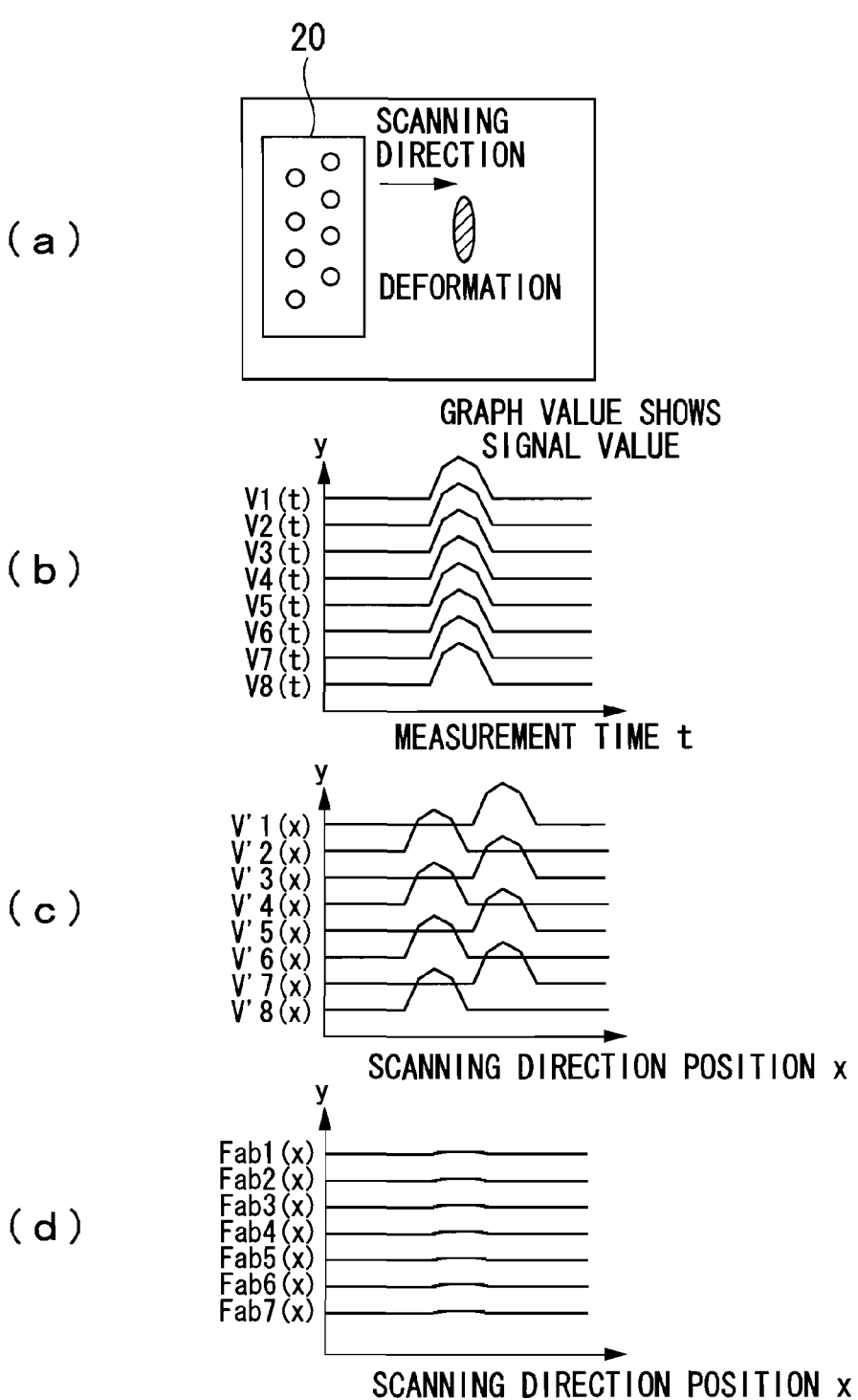
FIG. 8 is a diagram for explaining the processing executed by the processing device according to the second embodiment of the present invention.

For example, in the case in which a deformation, instead of a defect, occurs as shown in FIG. 8(a), as in the first embodiment described above, effects of the deformation simultaneously appear in the integrated flaw-detection sensors 11a1 to 11b4, and, as shown in FIG. 8(b), noise occurs at the same time in the detection signals V1(t) to V8(t) from the individual flaw-detection sensors 11a1 to 11b4. Then, the sensor-position corrected signals V'1(x) to V'8(x) corresponding to the detection signals V1(t) to V8(t) take waveforms like those shown in FIG. 8(c). When the filtering signals Fab1(x) to Fab7(x) are subsequently created from the sensor-position corrected signals V'1(x) to V'8(x) by comparing the adjacent signals with each other, the filtering signals take waveforms like those shown in FIG. 8(d). In this way, when a deformation occurs, noise in the adjacent sensor-position corrected signals occurs at positions that are different from each other, as shown in FIG. 8(c); therefore, such noise is attenuated in the filtering signals.

As described above, with the flaw-detection apparatus and the flaw-detection method according to this embodiment, the flaw-detection sensor groups, each of which is formed of two flaw-detection sensors, are further arranged in the direction perpendicular to the scanning direction to form the flaw-detection sensor unit 20, and a defect is detected on the basis of the detection signals detected by the individual flaw-detection sensors that constitute the flaw-detection sensor unit 20; therefore, flaw detection can be performed efficiently. Because flaw detection is performed by using the detection signals from all of the flaw-detection sensors, without having to provide sensors, etc. dedicated to detecting a deformation or the like, it is possible to perform efficient, high-precision flaw detection with a simple configuration.

With this embodiment, because the filtering signals are created from the adjacent sensor-position corrected signals, there is a problem in that only seven filtering signals Fab1(x) to Fab7(x) can be obtained even though eight flaw-detection sensors are provided. Specifically, assuming the Y-direction positions where flaw-detection signals Vi(t) (i=1, 2, . . . ) are measured to be Yi, the filtering signal Fab1(x) is a filtering signal whose Y-direction position is (Y1+Y2)/2, that is, the mid-point between Y1 and Y2, and Fab2(x) is also a filtering signal whose Y-direction position is (Y2+Y3)/2; therefore, there is a problem in that the filtering signals Fab1(x) to Fab7(x) do not correspond to the passing positions of the individual flaw-detection sensors 11a1 to 11b4.

Figure 9:
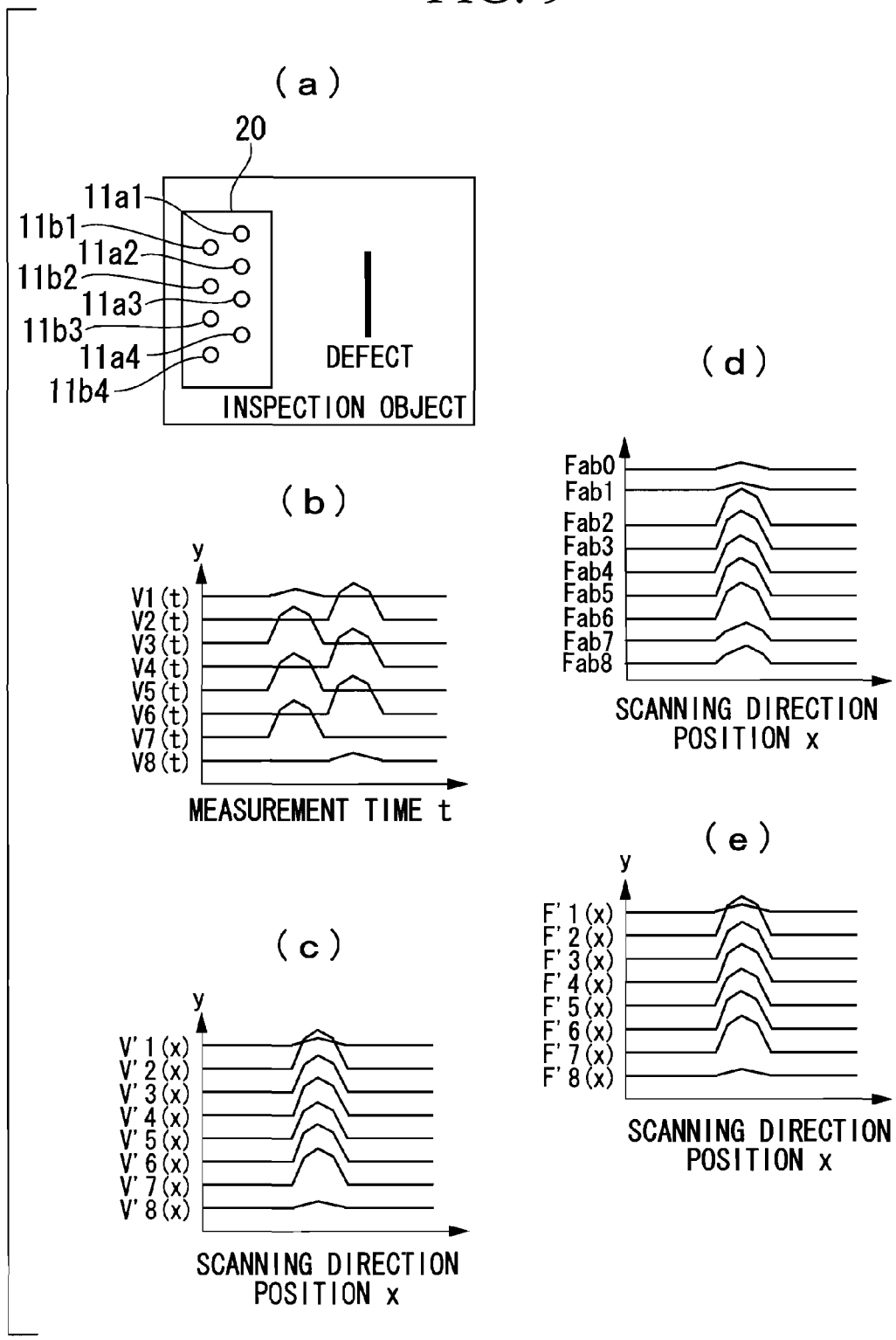
FIG. 9 is a diagram for explaining other processing executed by the processing device according to the second embodiment of the present invention.

In order to eliminate such a problem, signals F'1(x) to F'8(x) for which the sampling positions of the filtering signals Fabi(x) are interpolated so as to be matched with the sampling positions of the flaw-detection signals may be employed as filtering signals. The interpolation may be a general linear interpolation. For processing of the Y-direction end-points in the case in which there is no flaw-detection signal for adjacent regions, Fab0=Fab1 and Fab8=Fab7 are assumed for the two end-points under the condition of end-point signal continuity, as shown in FIG. 9(d), and the interpolation may be performed by using these. In the case in which the flaw-detection signals for adjacent regions are obtained with multiple scanning, lattice scanning, etc., the processing for the end points may be performed by using the signals for the adjacent regions.

{Third Embodiment}

Next, a flaw-detection apparatus and a flaw-detection method according to a third embodiment of the present invention will be described.

Figure 10:
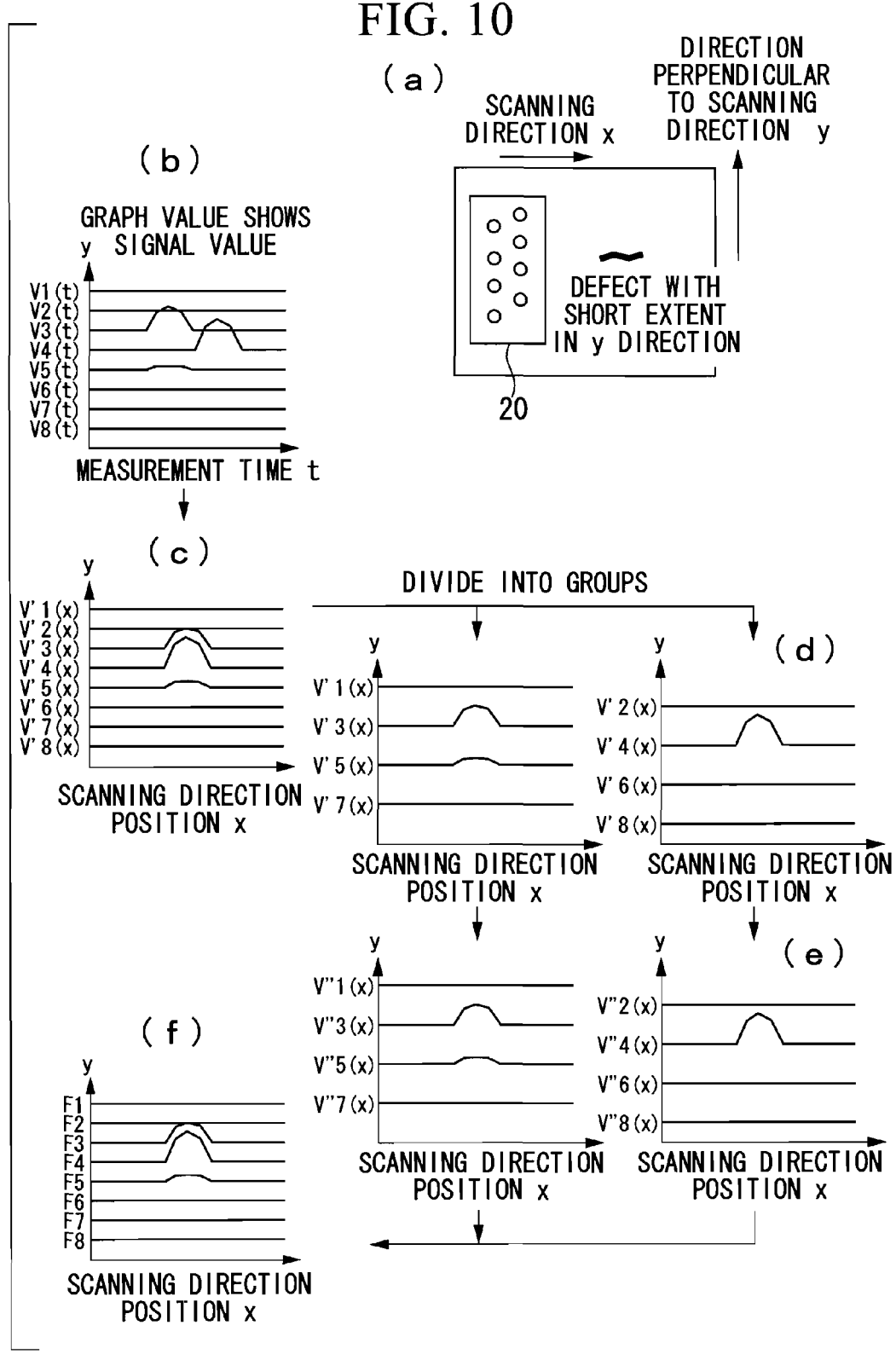
FIG. 10 is a diagram for explaining processing executed by a processing device according to a third embodiment of the present invention.

The flaw-detection apparatus and the flaw-detection method according to this embodiment are for performing flaw detection suitable for detecting a defect in which the length in the direction perpendicular to the scanning direction is extremely short, as in a defect occurring along the scanning direction, as shown in FIG. 10.

In the following, the flaw-detection apparatus and the flaw-detection method according to this embodiment will be described mainly with regard to differences from the second embodiment described above.

Because the flaw-detection apparatus according to this embodiment has a device configuration substantially similar to that of the second embodiment described above, detailed descriptions of the configuration thereof will be omitted.

For example, in the case in which a defect occurring along the scanning direction is assumed, as shown in FIG. 10(a), the detection signals detected by the individual flaw-detection sensors 11a1 to 11b4 take waveforms like those shown in FIG. 10(b). Specifically, of the eight flaw-detection sensors, the defect is detected only by some of the flaw-detection sensors. The processing device individually determines the sensor-position corrected signals from such detection signals. As a result, the sensor-position corrected signals like those shown in FIG. 10(c) are individually determined.

The processing device subsequently divides these sensor-position position corrected signals into groups in accordance with the placement positions of the flaw-detection sensors. For example, in the case in which it is assumed that the scanning direction is the x-axis direction and that the direction perpendicular to the scanning direction is the y-axis direction, the flaw-detection sensors whose placement positions have the same x-coodinate value are treated as one group. accordingly, the eight flaw-detection sensors 11a1 to 11b4 are divided into a group formed of the flaw-detection the flaw-detection sensors 11a1, 11b2, 11b4. The individual sensor-position corrected signals after division into group are shown in Fig. 10(d).

The processing device subsequently performs y-axis-direction-drift removal for the sensor-position corrected signals in each group, wherein signals having similar characteristics that occur at the same x-axis direction positions are removed. In the signal groups in the individual groups shown in FIG. 10(d), because closely-located signals in the groups do not show similar trends, drift-removed signals V"1(x) to V"8(x) are the same as the signals shown in FIG. 10(d), as shown in FIG. 10(e). The processing device subsequently obtains combined signal F1 to F8 shown in FIG. 10(f) by combining the drift-removed signals in the individual divided groups into one signal, and detects the defect on the basis of the combined signals F1 to F8. As a result, because signals appear only for the signals F3 to F5, it can be determined that the defect occurs at the positions of the flaw-detection sensors that correspond to the signals F3 and F5.

Figure 11:
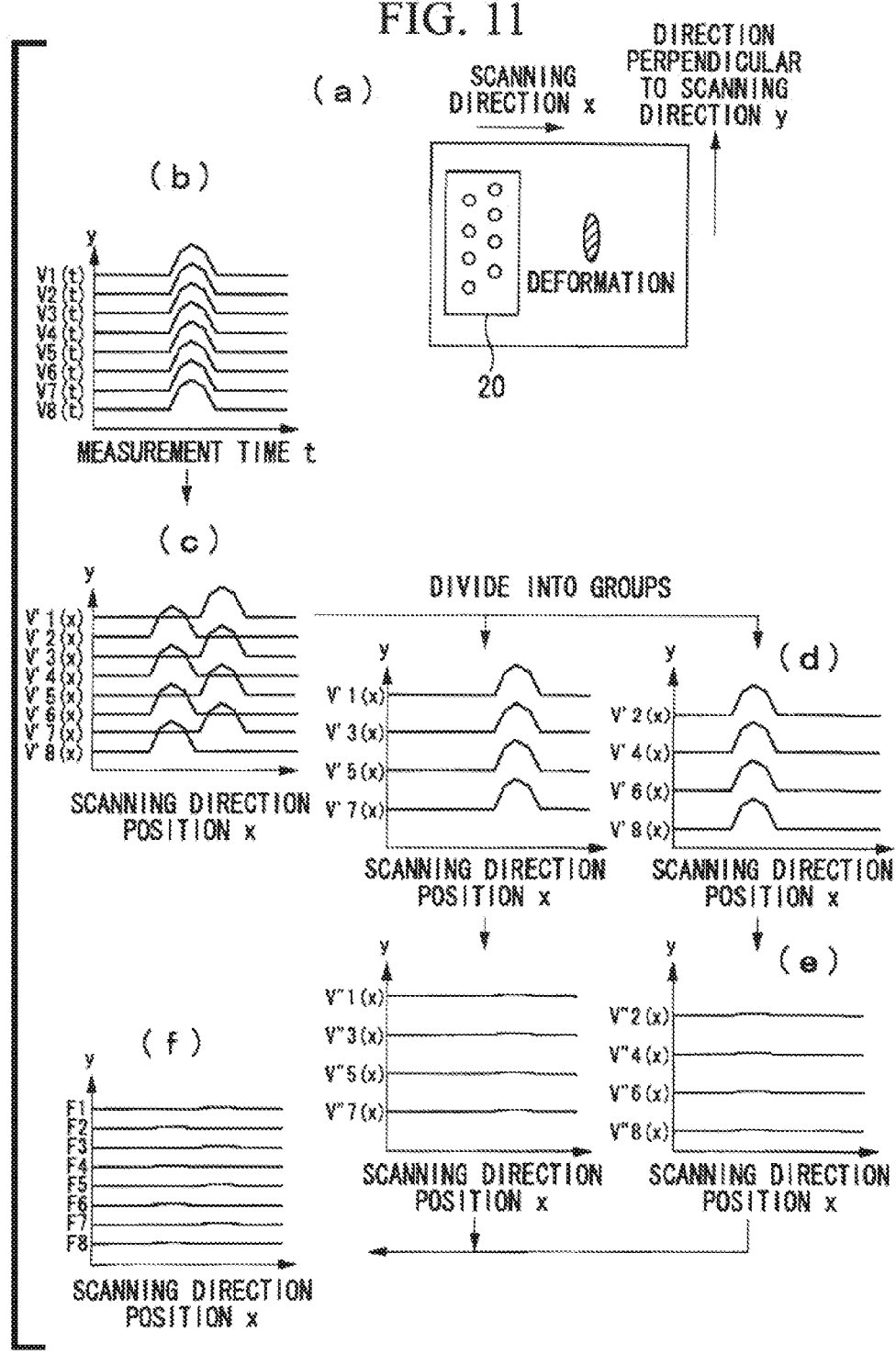
FIG. 11 is a diagram for explaining the processing executed by the processing device according to the third embodiment of the present invention.

In the case in which a deformation, instead of the defect described above, occurs, as shown in FIG. 11(a), the orientation change in the flaw-detection sensor unit 20 due to the influence of the deformation simultaneously occurs in all of the flaw-detection sensors that constitute the flaw-detection sensor unit 20; therefore, for example, the sensor-position corrected signals divided into the individual groups take waveforms like those shown in FIG. 11(d). In this way, in the case of the deformation, the same trends (characteristics) appear in the closely-located signals in the individual groups. Therefore, the Y-axis-direction-drift removed signals take waveforms like those shown in FIG. 11(e), and the noise components are removed. Then, the combined signals F1 to F8 like those shown in FIG. 11(f) are obtained by combining the drift-removed signals into one signal, and erroneous defect detection due to noise caused by the deformation can be prevented.

As described above, with the flaw-detection apparatus and the flaw-detection method according to this embodiment, it is possible to effectively detect, with a simple configuration, a defect having a short width that occurs along the scanning direction of the flaw-detection sensor unit.

Figure 12:
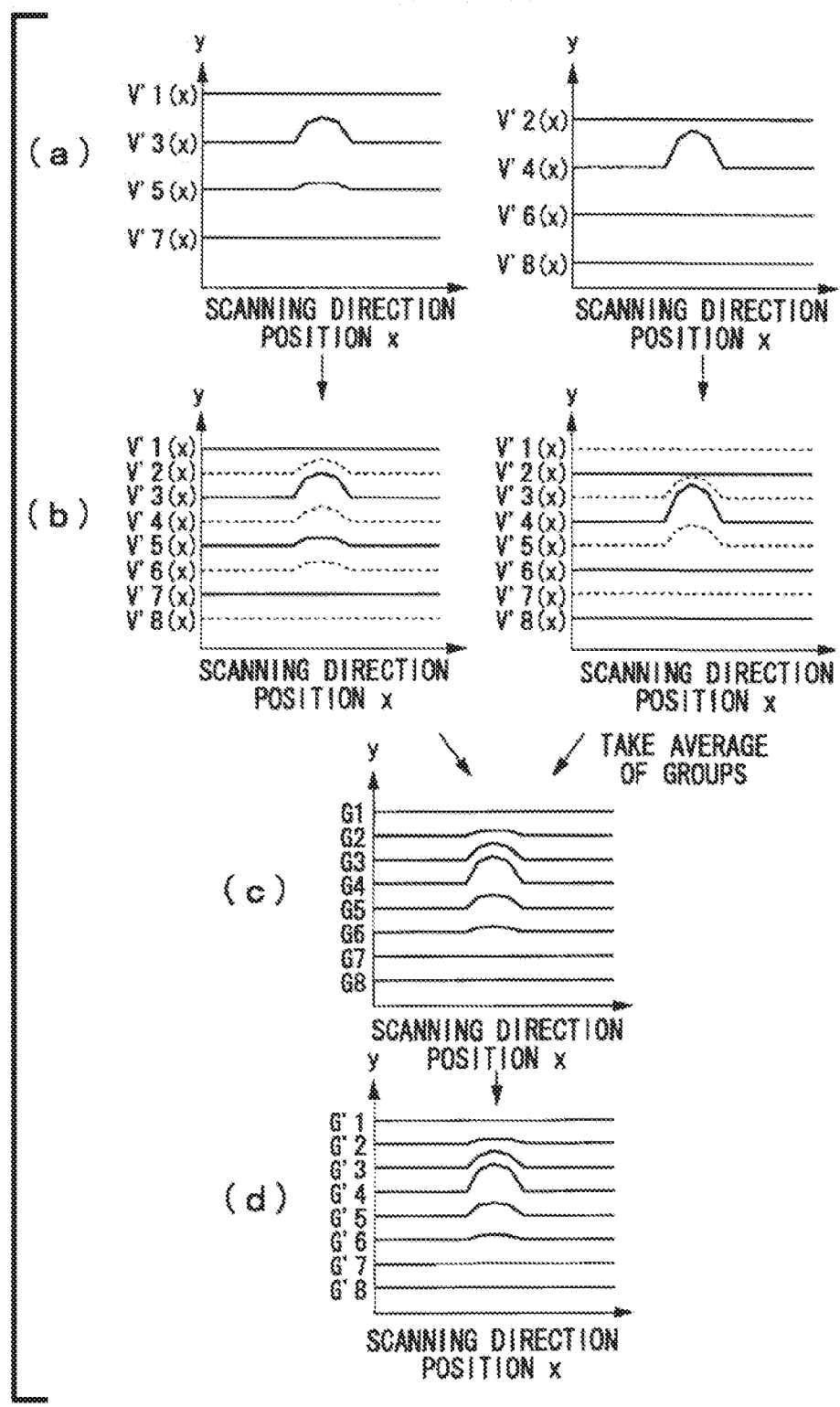
FIG. 12 is a diagram for explaining other processing executed by the processing device according to the third embodiment of the present invention.
Figure 13:
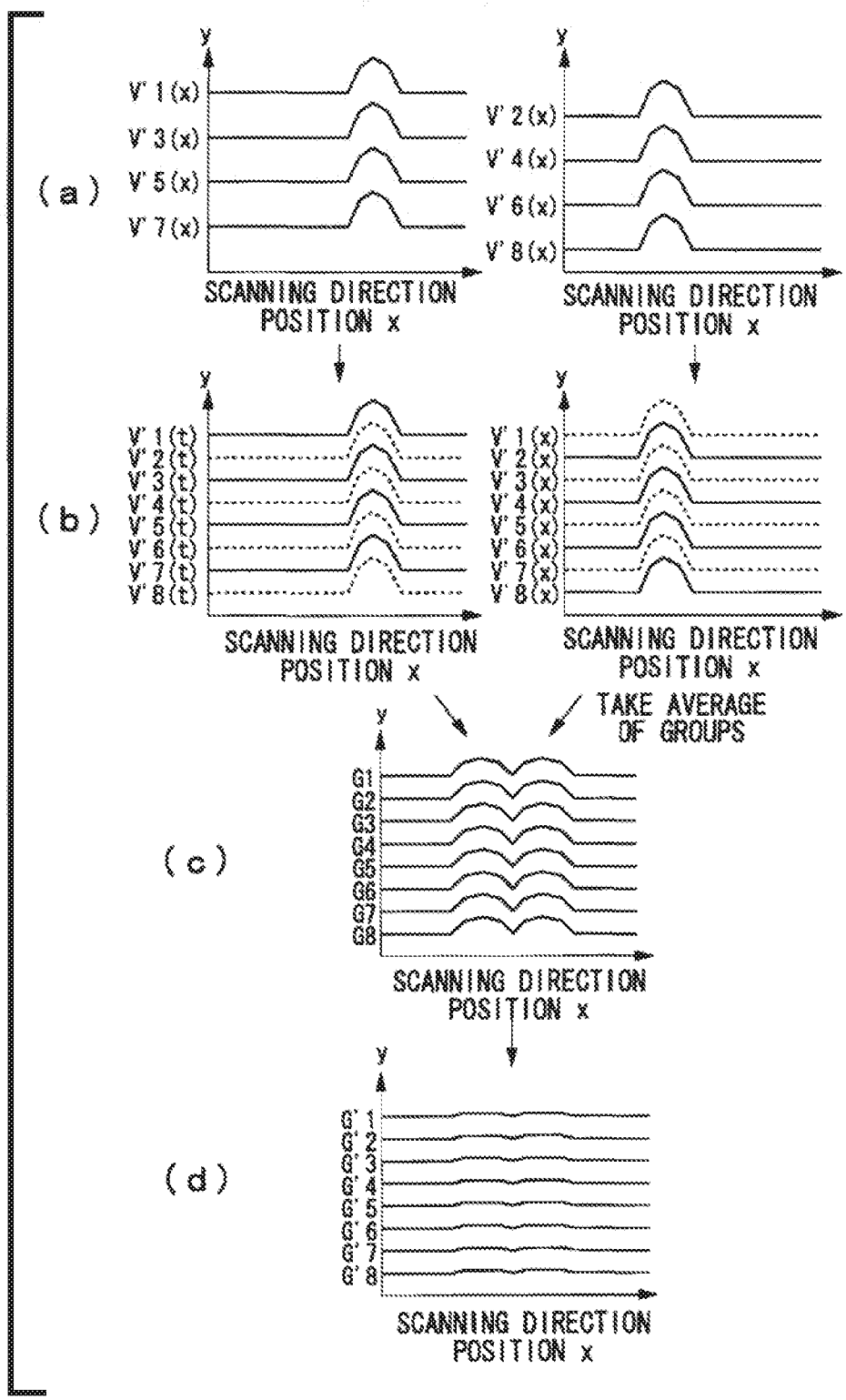
FIG. 13 is a diagram for explaining the other processing executed by the processing device according to the third embodiment of the present invention.

In the embodiment described above, because the sensor-position corrected signals obtained with the individual flaw-detection sensors are processed by dividing them into groups, there is a problem in that, as in the example shown in FIG. 11(f), residual components of the noise signals form discontinuous signals between the groups in the y-axis direction. Therefore, as shown in FIG. 12(b) and FIG. 13(b), decimated signals (signals shown by dotted lines in FIG. 12(b) and FIG. 13(b)) may be simulated by performing linear interpolation of the sensor-position corrected signals in the individual groups at y-axis direction positions in the opposing groups, and individual combined signals G1 to G8 may be created by taking averages of these signals in the individual groups (see FIG. 12(c) and FIG. 13(c)). Then, the Y-axis-direction drift removal may be applied to the combined signals G1 to G8 (see FIG. 12(d) and FIG. 13(d)), and the defect may be detected on the basis of processed combined signals G'1 to G'8.

By doing so, for example, in the case in which a defect occurs along the scanning direction, like the one shown in FIG. 10(a), changes due to the defect appear as shown in FIG. 12(d), and, in the case in which a deformation like the one shown in FIG. 11(a) occurs, the residual signals from which noise caused by the deformation has been removed can be converted into signals that are smooth in the y-axis direction, as shown in FIG. 13(d).

Although the cases in which flaw detection is performed by employing two or more flaw-detection sensors have been described in the individual embodiments described above, for example, as shown in FIG. 14(a) and FIG. 14(b), an inspection object may be two-dimensionally scanned by scanning a single flaw-detection sensor 11a in the x-axis direction and the y-axis direction. In this case, of the detection signals detected by the flaw-detection sensor, the signal values detected at substantially the same position should be compared with each other; filtering signals should be created, in which the signal values for the positions where the two signal values have substantially the same value are amplified relative to the signal values for the positions where the two signal values do not have substantially the same value; and the defect in the inspection object should be detected on the basis of the filtering signals. The method of creating the filtering signals is the same as that in the first embodiment described above.

Figure 15:
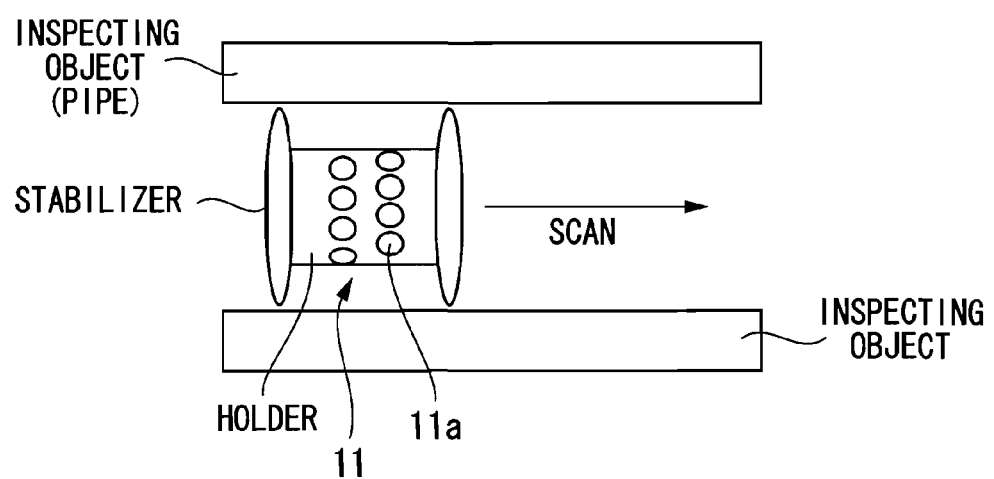
FIG. 15 is a diagram showing a configuration example of the flaw-detection apparatus according to the present invention.

Although cases in which a defect that occurs inside or at a surface of the inspection object is detected by scanning the flaw-detection sensors at the surface of the inspection object have been described in the individual embodiments described above, it is also possible to employ the flaw-detection apparatus and the flaw-detection method according to the present invention in a flaw-detection apparatus that performs non-contact scanning of the interior of a pipe, as shown in FIG. 15.

REFERENCE SIGNS LIST 1 flaw-detection apparatus
11 flaw-detection sensor group
11a, 11a1 to 11a4, 11b, 11b1 to 11b4 eddy-current flaw-detection sensor
12 driving device
13 flaw detector
14 storage device
15 processing device
20 flaw-detection sensor unit

The invention claimed is:
1. A flaw-detection apparatus comprising:
 a flaw-detection sensor unit in which a plurality of flaw-detection sensors of identical type are arranged substantially in one row at intervals along a scanning direction;
 a driving device that drives the flaw-detection sensor unit along the scanning direction;
 a storage device that records detection signals detected by the flaw-detection sensors, respectively; and
 a processing device that detects a defect in an inspection object on the basis of the detection signals recorded in the storage device;
 wherein each of the flaw-detection sensors is an eddy-current flaw-detection sensor, and
 wherein the processing device
  obtains a plurality of sensor-position corrected signals corresponding to the detection signals detected by the flaw-detection sensors, respectively, by convert- ing the detection signals which are time-series signals to signals for scanning-direction positions, compares signal values, among the sensor-position corrected signals, taken at substantially the same scanning positions, respectively, generates a filtering signal such that values of the filtering signal at the scanning position of which a plurality of the values of the sensor-position corrected signals are substantially the same are enhanced further than values of the filtering signal at the scanning position of which a plurality of the values of the sensor-position corrected signals are not substantially the same, and detects the defect in the inspection object by using the filtering signal, wherein the processing device further detects substantially similar signal values at a same time, but at the different scanning positions and determines that the detected signals are not defect signals so as to filter noise components due to causes other than the defect when the plurality of flaw detection sensors, which are integrally attached to each other, experience a similar shift in a Z-axis direction during scanning, the Z-axis direction being a direction perpendicular to a scanning surface of the inspection object.

2. The flaw-detection apparatus according to claim 1, wherein, the processing device generates the filtering signal by taking a cross-correlation among the sensor-position corrected signals, by taking an average among the sensor-position corrected signals, or by taking a smallest value among the absolute values of the signal values of the sensor-position corrected signals at each of the scanning position.

3. The flaw-detection apparatus according to claim 2, wherein, assuming that the scanning direction is an x-axis direction and that the direction perpendicular to the scanning direction is a y-axis direction, the flaw-detection sensor unit has a plurality of flaw-detection sensor groups disposed at intervals along the x-axis, and wherein, each of the flaw-detection sensor groups has a plurality of the flaw-detection sensor which are disposed at intervals along the y-axis.

4. The flaw-detection apparatus according to claim 3, wherein, each of the flaw-detection sensors of at least one of the flaw-detection sensor groups is disposed so as to individually take y-coordinate values different from those of other flaw-detection sensor groups;

wherein, the processing device generates a plurality of the filtering signals by comparing the sensor-position corrected signals from the flaw-detection sensors whose y-coordinate values are adjacent to each other, and detects the defect in the inspection object using the filtering signals.

5. A flaw-detection apparatus comprising:

a flaw-detection sensor unit having a plurality of flaw-detection sensor groups which are disposed at intervals along a scanning direction, wherein each of the flaw-detection sensor groups has a plurality of a flaw-detection sensors of identical type which are disposed at intervals along the direction perpendicular to the scanning direction;

a driving device that drives the flaw-detection sensor unit along the scanning direction;

a storage device that records detection signals detected by the flaw-detection sensors, respectively; and a processing device that detects a defect in an inspection object on the basis of the detection signals recorded in the storage device;

wherein each of the flaw-detection sensors is an eddy-current flaw-detection sensor, wherein, assuming that the scanning direction is an x-axis direction and that the direction perpendicular to the scanning direction is a y-axis direction, each of the flaw-detection sensors of at least one of the flaw-detection sensor groups is disposed so as to individually take y-coordinate values different from those of other flaw-detection sensor groups; and wherein, the processing device obtains a plurality of sensor-position corrected signals corresponding to the detection signals detected by the flaw-detection sensors, respectively, by converting the detection signals which is time-series signals to signals for scanning-direction positions, performs interpolation so that each group consisting of a plurality of the sensor-position corrected signals which corresponds to each of a plurality of the flaw-detection sensor groups has sensor-position corrected signals detected at the same y-axis coordinate, generates combined signals by combining the sensor-position corrected signals detected at the same y-axis coordinate value, and detects the defect in the inspection object on the basis of the combined signals, wherein the processing device further detects substantially similar signal values at a same time, but at the different scanning positions and determines that the detected signals are not defect signals so as to filter noise components due to causes other than the defect when the plurality of flaw detection sensors belonging to each of the flaw-detection sensor groups, which are integrally attached to each other, experience a similar shift in a Z-axis direction during scanning, the Z-axis direction being a direction perpendicular to a scanning surface of the inspection object.

6. A flaw-detection method comprising:

driving a flaw-detection sensor unit along a scanning direction, the flaw-detection sensor unit having a plurality of flaw-detection sensors of identical type which are arranged in substantially in one row at intervals along the scanning direction, each of the flaw-detection sensors being an eddy-current flaw-detection sensor;

recording detection signals detected by the flaw-detection sensors, respectively;

obtaining a plurality of sensor-position corrected signals corresponding to the detection signals detected by the flaw-detection sensors, respectively, by converting the detection signals which are time-series signals to signals for scanning-direction positions, comparing signal values, among the sensor-position corrected signals, taken at substantially the same scanning positions, respectively, generating a filtering signal such that values of the filtering signal at the scanning position of which a plurality of the values of the sensor-position corrected signals are substantially the same are enhanced further than values of the filtering signal at the scanning position of which a plurality of the values of the sensor-position corrected signals are not substantially the same, detecting the defect in the inspection object by using the filtering signal, detecting substantially similar signal values at a same time, but at the different scanning positions when the plurality of flaw detection sensors, which are integrally attached to each other, experience a similar shift in a Z-axis direction during scanning, the Z-direction being a direction perpendicular to a scanning surface of the inspection object, and determining that the detected signals are not defect signals so as to filter noise components due to causes other than the defect.

7. A flaw-detection method for detecting a defect in the inspection object by using a flaw-detection sensor unit having a plurality of flaw-detection sensor groups which are disposed at intervals along a scanning direction, wherein each of the flaw-detection sensor groups has a plurality of flaw-detection sensors of identical type which are disposed at intervals along the direction perpendicular to the scanning direction, wherein each of the flaw-detection sensors is an eddy-current flaw-detection sensor, and wherein, assuming that the scanning direction is an x-axis direction and that the direction perpendicular to the scanning direction is a y-axis direction, each of the flaw-detection sensors of at least one of the flaw-detection sensor groups is disposed so as to individually take y-coordinate values different from those of other flaw-detection sensor groups, the flaw-detection method comprising:

driving the flaw-detection sensor unit along the scanning direction;

recording detection signals detected by the flaw-detection sensors, respectively;

obtaining a plurality of sensor-position corrected signals corresponding to the detection signals detected by the flaw-detection sensors, respectively, by converting the detection signals which is time-series signals to signals for scanning-direction positions, performing interpolation so that each group consisting of a plurality of the sensor-position corrected signals which corresponds to each of the plurality of the flaw-detection sensor groups has sensor-position corrected signals detected at the same y-axis coordinate, generating combined signals by combining the sensor-position corrected signals detected at the same y-axis coordinate value, detecting the defect in the inspection object on the basis of the combined signal, detecting substantially similar signal values at a same time, but at the different scanning positions when the plurality of flaw detection sensors, which are integrally attached to each other, experience a similar shift in a Z-axis direction during scanning, the Z-direction being a direction perpendicular to a scanning surface of the inspection object, and determining that the detected signals are not defect signals so as to filter noise components due to causes other than the defect.

\* \* \* \* \*